United States Patent [19]

Baker et al.

[11] Patent Number: 5,527,817
[45] Date of Patent: Jun. 18, 1996

[54] SULPHATE SALT OF A SUBSTITUTED TRIAZOLE, PHARMACEUTICAL COMPOSITIONS THEREOF, AND THEIR USE IN THERAPY

[75] Inventors: Raymond Baker, Much Hadham, England; Victor G. Matassa, Rome, Italy; Alexander R. Guiblin, Harlow, England; Kendal G. Pitt, Hatfield, England; Leslie J. Street, Harlow, England; Carole Olive; David E. Storey, both of Lansdale, Pa.

[73] Assignee: Merck Sharp & Dohme Limited, Hoddesdon, England

[21] Appl. No.: 350,760

[22] Filed: Dec. 7, 1994

Related U.S. Application Data

[63] Continuation of Ser. No. 69,241, May 28, 1993, abandoned.

[30] Foreign Application Priority Data

Jun. 5, 1992 [GB] United Kingdom .................. 9211903
Apr. 7, 1993 [GB] United Kingdom .................. 9307306

[51] Int. Cl.$^6$ ........................ A61K 31/41; C07D 403/06
[52] U.S. Cl. ........................................ 514/383; 548/266.4
[58] Field of Search ........................ 548/266.4; 514/383

[56] References Cited

U.S. PATENT DOCUMENTS 5,298,520  3/1994  Baker et al. .......................... 514/383

FOREIGN PATENT DOCUMENTS

0313397A1  4/1989  European Pat. Off. .
0490689A1  12/1991  European Pat. Off. .
0497512A2  8/1992  European Pat. Off. .

OTHER PUBLICATIONS

G. R. Martin et al., "Analysis of the 5-HT receptor, etc" 342, 8, 111 (1990).

*Primary Examiner*—Patricia L. Morris
*Attorney, Agent, or Firm*—Robert J. North; Melvin Winokur

[57] ABSTRACT

The sulphate salt of N,N-dimethyl-2-[5-(1,2,4-triazol-1-yl-methyl)-1H-indol-3-yl]ethylamine is a selective agonist of 5-HT$_1$-like receptors and is therefore useful in the treatment of clinical conditions, in particular migraine and associated disorders, for which a selective agonist of these receptors is indicated.

15 Claims, No Drawings

SULPHATE SALT OF A SUBSTITUTED TRIAZOLE, PHARMACEUTICAL COMPOSITIONS THEREOF, AND THEIR USE IN THERAPY

CROSS REFERENCE TO RELATED APPLICATIONS

The instant case is a continuation application of Ser. No. 08/069,241, filed May 28, 1993, now abandoned.

The present invention relates to a particular salt of a pharmaceutically active agent. More particularly, the invention relates to the sulphate salt of a substituted triazole derivative which acts on 5-hydroxytryptamine (5-HT) receptors, being a selective agonist of so-called "5-HT$_1$-like" receptors. This compound is therefore useful in the treatment of clinical conditions for which a selective agonist of these receptors is indicated.

5-HT$_1$-like receptor agonists which exhibit selective vasoconstrictor activity have recently been described as being of use in the treatment of migraine (see, for example, A. Doenicke et al., *The Lancet*, 1988, Vol. 1, 1309–11). The salt of the present invention, exhibiting selective 5-HT$_1$-like receptor agonist activity, is accordingly of particular use in the treatment of migraine and associated conditions, e.g. cluster headache, chronic paroxysmal hemicrania, headache associated with vascular disorders, tension headache and paediatric migraine.

EP-A-0497512, published on 5th Aug. 1992, describes a class of substituted imidazole, triazole and tetrazole derivatives which are stated to be selective agonists of 5-HT$_1$-like receptors and hence to be of particular use in the treatment of migraine and associated conditions.

The present invention provides the sulphate salt of N,N-dimethyl-2-[5-(1,2,4-triazol-1-ylmethyl)-1H-indol-3-yl]ethylamine. Specifically, the invention provides N,N-dimethyl-2-[5-(1,2,4-triazol-1-ylmethyl)-1H-indol-3-yl]ethylamine sulphate salt (2:1) of structural formula I:

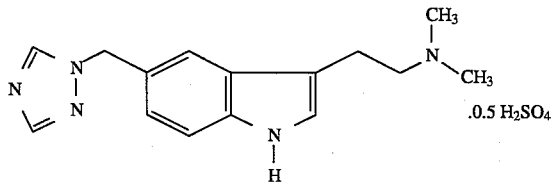

and pharmaceutically acceptable solvates, including hydrates, in particular the 0.7 hydrate, thereof.

Pharmaceutically acceptable salts of N,N-dimethyl-2-[5-(1,2,4-triazol-1-ylmethyl)-1H-indol-3-yl]ethylamine are generically encompassed within the scope of EP-A-0497512. Indeed, the oxalate hemihydrate, succinate and benzoate salts thereof are specifically disclosed in EP-A-0497512. However, nowhere in EP-A-0497512 is there a specific disclosure of the particular salt of structural formula I above or pharmaceutically acceptable solvates thereof.

The salt of structural formula I above has been found to possess advantageous properties in several respects which make it particularly suitable for use as a pharmaceutical agent. For example, unlike many drugs which are known to have an unpleasant taste, the salt of formula I has been found to be relatively free from flavour.

In another aspect, therefore, the present invention provides a pharmaceutical composition comprising the sulphate salt of formula I above or a pharmaceutically acceptable solvate thereof in association with one or more pharmaceutically acceptable carriers.

The compositions in accordance with the invention are suitably in unit dosage forms such as tablets, pills, capsules, powders, granules, sterile solutions or suspensions, metered aerosol or liquid sprays, drops, ampoules, auto-injector devices or suppositories; for oral, parenteral, intranasal, sublingual or rectal administration, or for administration by inhalation or insufflation. Formulation of the compositions according to the invention can conveniently be effected by methods known from the art, for example as described in *Remington's Pharmaceutical Sciences*, 17th Ed., 1985.

For example, for preparing solid compositions such as tablets, the active ingredient is mixed with a pharmaceutical carrier, e.g. conventional tableting ingredients such as microcrystalline cellulose, corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of the salt of formula I above. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention.

The liquid forms in which the salt of the present invention may be incorporated for administration orally, intranasally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compositions may be administered on a regimen of 1 to 4 times per day.

In one embodiment of the composition according to the present invention is provided a pharmaceutical composition in solid form adapted for sublingual administration, comprising the salt of formula I as defined above or a pharmaceutically acceptable solvate thereof; one or more pharmaceutically acceptable buffering agents capable of imparting to the buccal cavity following administration a pH of at least 7.5; and one or more pharmaceutically acceptable excipients.

Although the sublingual region of the oral cavity is small in area, it is rich in blood vessels and lymphatics. Accordingly, for certain molecules absorption is rapid and a systemic therapeutic effect can be achieved very quickly. An additional advantage of the sublingual route is that drugs taken sublingually may enter the systemic circulation directly, avoiding passage through the liver where they might otherwise be metabolised. However, the great majority of commercially available drugs are amines, and are consequently basic. In the physiological environment of the oral cavity, where the native pH will be in the order of 6.2 to 7.4, the ionisation state of such basic drugs is detrimental to an acceptable rate of absorption thereof from the buccal cavity.

It is known from the literature (see, for example, Rathbone and Hadgraft, *Int. J. Pharmaceutics*, 1991, 74, 9–24)

that increasing the pH of buccal formulations may increase the buccal absorption of basic drugs contained therein. For this reason, the sublingual formulation of the present invention incorporates a buffer capable of imparting to the buccal cavity following administration a pH of at least 7.5.

Examples of typical compositions in solid form which may be adapted for sublingual administration include tablets, especially freeze-dried tablets such as the Zydis$^{(R)}$ system described in U.S. Pat. No. 4,371,516; capsules, including dry filled capsules, liquid filled soft gelatin capsules and hard gelatin capsules; powders; and granules. Preferably, the sublingual composition in accordance with the invention is in tablet form.

The finished sublingual composition according to the invention will be of any convenient size and shape compatible with sublingual administration. Where the composition is in tablet form, the tablet will typically weigh from 50 to 500 mg. Preferably, the weight of the tablet is in the region of 220 mg.

The sublingual composition according to the invention incorporates one or more pharmaceutically acceptable buffering agents capable of imparting to the buccal cavity following administration a pH of at least 7.5. As mentioned above, it is known that buccal absorption of basic drugs may be enhanced if the pH of the oral cavity is increased. The solid sublingual formulation of the present invention may therefore possess the advantage that when it is placed in the buccal cavity the pH of the mouth is increased and absorption of drug may thereby be enhanced relative to that which would be achieved from a corresponding unbuffered formulation.

There is in principle no restriction on the nature of the buffering agent employed in the sublingual composition according to the invention, provided that it is pharmaceutically acceptable and capable of ensuring that the pH of the buccal cavity following administration is at least 7.5. The skilled person will be aware of a variety of buffering agents which may suitably be employed in this context. Examples of appropriate buffering agents include glycine/sodium hydroxide, sodium carbonate, sodium bicarbonate, and mixtures thereof. A preferred buffer system comprises a mixture of sodium carbonate and sodium bicarbonate.

The amount of buffering agent to be incorporated into the sublingual composition according to the invention will largely be dependent upon the desired pH of the final composition. As will be appreciated, it is important to ensure that the amount of buffering agent employed is such as to maintain the upper pH level of the buccal cavity following administration within physiologically acceptable limits. For example, where a buffer system comprising a mixture of sodium carbonate and sodium bicarbonate is employed, it has been found desirable to maintain the pH of the composition according to the invention below about 9.6, since above this pH level a certain amount of buccal irritation is encountered, resulting in a burning sensation within the mouth. Thus, where a mixture of sodium carbonate and sodium bicarbonate is employed, the amount of sodium carbonate in the final composition, computed as anhydrous sodium carbonate or as an equivalent amount of hydrated sodium carbonate, will suitably be from 5 to 20%, preferably about 10%, by weight; and the amount of sodium bicarbonate will suitably be from 15 to 35%, preferably 30%, by weight of the final composition.

The pharmaceutically acceptable excipients incorporated into the sublingual composition according to the invention may suitably be those conventionally employed in connection with sublingual formulations. Representative excipients are described, for example, in *Remington's Pharmaceutical Sciences*, supra, and typically include binders such as corn starch; lubricants such as magnesium stearate; compression aids such as cellulose, lactose and mannitol; and disintegrants such as sodium starch glycolate and sodium carboxymethylcellulose.

Since the sublingual composition in accordance with the invention is adapted for administration by the oral route, the taste of the finished composition is a factor which needs to be taken into consideration. Many buffering agents have an unpleasant taste. For example, a buffer system consisting of a mixture of sodium carbonate and sodium bicarbonate has been found to impart an unpleasant taste to formulations containing this system. For this reason, it may be advantageous to incorporate a sweetening and/or flavouring agent into the sublingual composition according to the invention.

Suitable sweetening agents include water-soluble natural sweeteners such as monosaccharides, disaccharides and polysaccharides, for example xylose, ribose, glucose, mannose, galactose, fructose, dextrose, sucrose, invert sugar, maltose, partially hydrolyzed starch, or corn syrup solids and sugar alcohols such as sorbitol, xylitol, mannitol, dihydrochalcone, glycyrrhizin and *stevia rebaudiana* (stevioside); water-soluble artificial sweeteners such as the soluble saccharin salts, i.e. sodium or calcium saccharin salts, cyclamate salts, the free acid form of saccharin, and the synthetic sweetener 3,4-dihydro-6-methyl-1,2,3 -oxathiazin-4-one 2,2-dioxide, particularly the potassium (acesulfame-K), sodium and calcium salts thereof; dipeptide-based sweeteners such as L-aspartyl-L-phenylalanine methyl ester; and mixtures thereof. A preferred sweetening agent is saccharin sodium.

In general, the amount of sweetening agent employed will vary with the desired sweetness of a particular composition and, if necessary, the extent of unpleasant flavour which it is desires to mask. By way of example, where the sweetening agent employed is saccharin sodium, the amount thereof incorporated is suitably from 0 to 10% by weight of the final sublingual composition, and preferably about 5% by weight.

Examples of flavouring agents useful for incorporation into the sublingual composition according to the invention include synthetic flavour oils, fruit essences and natural flavour oils derived from such sources as plants, leaves and flowers; as well as mixtures of the foregoing. Particular examples include spearmint oil, peppermint oil, cinnamon oil and oil of wintergreen (methyl salicylate); citrus oils derived from sources such as lemon, orange, grape, lime and grapefruit; fruit essences derived from sources such as apple, strawberry, cherry and pineapple; and extracts such as kola extract. A particular flavouring agent is Peppermint NAEFCO/P05.51.

As with the sweetening agent, the amount of flavouring agent employed is normally a matter of individual preference but will, in particular, be influenced by the extent of unpleasant flavour which, if necessary, it is desired to mask. In general, amounts of flavouring agent from 0 to 10% by weight of the final sublingual composition are suitable, with an amount of about 3% by weight being preferred.

If desired, a pharmaceutically acceptable colouring agent may suitably be incorporated into the sublingual composition according to the invention. A typical colouring agent is the internationally acceptable blue aluminium lake Blue FD&C No. 2. The colouring agent may suitably be incorporated into the finished composition in an amount of from 0 to 1.0%, preferably about 0.25%, by weight.

By judicious choice of the proportions of the individual components constituting the sublingual composition according to the invention, it is possible to achieve a final formulation capable of displaying the advantageous property of maintaining a pH of at least 7.5, preferably at least 9.0, in the buccal cavity for a prolonged period.

The sublingual composition in accordance with the present invention may conveniently be manufactured by a variety of standard procedures which will be familiar to the person skilled in the art. Typical well-known procedures include the direct compression method and the wet granulation method.

Oral compositions may be subject to certain drawbacks in the treatment of conditions such as migraine, because such conditions are often accompanied by nausea, which makes it difficult for a patient to tolerate an oral composition. Parenteral administration generally has the advantage of rapid absorption of drug, but this route of administration can be unacceptable to some patients, especially if the composition is presented in a form adapted for self-administration.

The salt of formula I has in fact been found to possess a surprisingly high solubility in water, rendering it especially amenable to the preparation of formulations, in particular intranasal formulations, which require relatively concentrated aqueous solutions of active ingredient. The solubility of the salt of formula I in water, expressed in terms of the free base, has been found to be approximately 170 mg/ml. This can be compared with, for example, the solubility of the benzoate salt of N,N-dimethyl-2-[5-(1,2,4-triazol-1-ylmethyl)-1H-indol,3-yl]ethylamine (Example 18 of EP-A-0497512), which under comparable conditions has been found to be approximately 40 mg/ml.

Moreover, the sulphate salt in accordance with the present invention has been found to exhibit an unexpectedly low tonicity. From theoretical considerations, the tonicity of a given solution, expressed as the osmolarity thereof in milliOsmols, can be derived by application of the following equation:

$$T = \frac{C \times 1000 \times N}{M}$$

where

T is the theoretical tonicity in mOsml;

C is the concentration of the solution in mg/ml;

N is the number of ions per salt molecule; and

M is the molecular weight of the salt.

Applying the above equation to the salt of formula I above, the theoretical tonicity of an aqueous solution thereof at a concentration of 189 mg/ml (equivalent to 160 mg/ml of free base) can be calculated as follows:

$$T = \frac{189 \times 1000 \times 3}{636.76} \text{ mOsml or } T = \underline{891} \text{ mOsml.}$$

However, when actually measured by conventional practical methods (for example by means of an osmometer utilising the well-known freezing-point depression procedure), the tonicity of an aqueous solution of the salt of formula I at a concentration of 189 mg/ml (equivalent to 160 mg/ml of free base) is in fact found to be only about 340 mOsml.

This unforeseen low tonicity of aqueous solutions of the sulphate salt according to the invention may be rationalised by one or more of a variety of mechanistic interpretations. One possible explanation may be that the ions of free base aggregate into micelles upon dissolution of the salt whereby the number of "particles" in solution will be reduced, thus effectively lowering the value of the parameter N in the theoretical tonicity equation above. Other mechanistic interpretations may, however, be equally plausible, and it is to be understood that none of these explanations should be construed as limiting the scope of the invention in any way.

The practical consequence of the low tonicity of solutions of the salt according to the invention relative to the predicted value is realised in a consequential lowering of local irritancy in those regions of the body to which such solutions are administered. This effect is particularly notable in those regions possessing especially sensitive membranes, such as the intranasal cavity. Thus, in view of this property, combined with its high solubility as noted above, the sulphate salt of formula I is ideally suited to the preparation of aqueous intranasal formulations.

The influence of tonicity on the irritant effect of ionic solutions can be illustrated with aqueous sodium chloride solutions of varying concentrations. Thus, an aqueous sodium chloride solution at a tonicity of 900 mOsml [cf. the theoretical tonicity of 891 mOsml for the salt of formula I above at a concentration of 189 mg/ml (equivalent to 160 mg/ml of free base)] when administered intranasally causes an appreciable tingling sensation. Such a solution is very hypertonic. On the other hand, the tolerability of an aqueous sodium chloride solution at a tonicity of 305 mOsml [cf. the observed actual tonicity of 340 mOsml for the salt of formula I above at a concentration of 189 mg/ml (equivalent to 160 mg/ml of free base)] when administered intranasally is completely acceptable. At a tonicity of 305 mOsml, an aqueous sodium chloride solution is isotonic. Thus, since the observed actual tonicity value for the sulphate salt according to the invention at a concentration of 160 mg/ml (expressed in terms of free base) is 340 mOsml this means that, at this concentration, an aqueous solution thereof is only very slightly hypertonic.

For the reasons discussed above, it can be appreciated that the salt according to the invention is particularly amenable to administration by the intranasal route. In a preferred embodiment of the composition according to the present invention, therefore, there is provided a pharmaceutical composition adapted for intranasal administration, which comprises the sulphate salt of formula I above or a pharmaceutically acceptable solvate thereof in association with one or more pharmaceutically acceptable carriers.

Intranasal formulations may generally be provided in liquid or dry powder forms. Satisfactory intranasal formulations must be sufficiently stable, chemically and physically, to be consistently dispensed in accurate metered doses, even after prolonged storage with potential temperature fluctuations of between 0° and 40° C. Accordingly, the active ingredient must be compatible with the excipients used in the formulation and should not aggregate in a manner which would result in a loss of accurate dose delivery, for example by precipitation from a liquid formulation or by caking of a powder formulation. To maximise retention of an intranasal formulation within the nasal passages of a patient after administration, particularly of a liquid formulation, it is desirable to deliver the unit dosage of active ingredient within a relatively small delivery volume, for example 50–200 µl, preferably about 100 µl. This may necessitate the use of high concentrations of medicament and highly soluble active ingredients are therefore advantageous. Clearly, an active ingredient must also be presented in a form which is readily absorbed through the nasal mucosa but which is unassociated with any adverse effects such as irritancy.

As indicated above, it has been found that for intranasal administration the salt according to the invention may advantageously be administered in the form of a solution.

Solutions will generally be aqueous; they may be prepared from water alone (for example sterile, pyrogen-free water), or from water and a pharmaceutically acceptable co-solvent (for example ethanol, propylene glycol, and polyethylene glycols such as PEG 400).

Such solutions may additionally contain other excipients such as preservatives (for example benzalkonium chloride and phenylethyl alcohol), buffering agents, tonicity-adjusting agents (for example sodium chloride), viscosity enhancing agents, absorption enhancers, flavouring agents (for example aromatic flavouring agents such as menthol, eucalyptol, camphor and methyl salicylate in amounts of from about 0.001 to about 0.5% w/w) and sweetening agents (for example saccharin or saccharin sodium in amounts of from about 0.01% w/w to about 10% w/w, preferably in the range of 0.01 to 2% w/w).

Preferably solutions according to the invention will be sterile and free from preservatives. Sterile formulations may be prepared by methods known in the art, for example by aseptic manufacture or sterilisation of bulk products.

Solutions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the patient administering an appropriate, predetermined volume of the solution. In the case of a spray this may be achieved for example by means of a metering atomising spray pump.

Intranasal administration may also be achieved by means of an aerosol formulation in which the compound is provided in a pressurised pack with a suitable propellant such as a chlorofluorocarbon (CFC), for example dichlorodifluoromethane, trichlorofluoromethane or dichlorotetrafluoroethane; a hydrofluorocarbon (HFC), for example 1,1,1,2-tetrafluoroethane or 1,1,1,2,3,3,3-heptafluoropropane; a hydrochlorofluorocarbon (HCFC), for example chlorodifluoromethane, 1,1,1-chlorodifluoroethane, 1,1-dichloro-2,2,2-trifluoroethane, 1-chloro-1,2,2,2-tetrafluoroethane or 1,1,1-dichlorofluoroethane; carbon dioxide; or other suitable gas. The dose of drug may be controlled by provision of a metered valve. Alternatively, a piezoelectric device may be employed in order to achieve the required spray.

Preferably a pharmaceutical composition adapted for intranasal administration which contains the salt according to the invention will be in the form of an aqueous solution.

Thus, the present invention also provides a substantially isotonic aqueous solution of the salt of formula I as defined above; as well as the use of such a solution in the preparation of pharmaceutical compositions adapted for intranasal administration.

Aqueous solutions of the salt of the present invention adapted for intranasal administration will suitably have a pH in the range 4 to 8. Preferably the pH of aqueous solutions of the salt according to the invention for intranasal administration will be between 5 and 7. At a concentration of 160 mg/ml (expressed in terms of free base), the pH of an aqueous solution of the sulphate salt of formula I above has been found to be approximately 5.8. This is particularly advantageous, since such solutions require no adjustment of pH prior to use. Solutions of more acidic salts, with pH values falling outside the acceptable range, will require adjustment of the pH by the addition of further excipients, in particular buffers, and this in turn will have a deleterious effect upon the pharmaceutical properties of the resulting solution owing to the concomitant increase in tonicity. Nevertheless, should adjustment of the pH of aqueous solutions of the salt of formula I be required, this can conveniently be effected by conventional means, such as by the controlled addition of a pharmaceutically acceptable acid or base.

It will be appreciated that aqueous solutions of the sulphate salt according to the invention may conveniently be prepared by dissolving the salt in water. Alternatively, such solutions may be obtained by mixing 1 molar equivalent of N,N-dimethyl-2-[5-(1,2,4-triazol-1-ylmethyl)-1H-indol-3-yl]ethylamine with 0.5 to 0.7 molar equivalents of concentrated sulphuric acid, preferably 0.5 molar equivalents of sulphuric acid, in water.

For intranasal administration, aqueous solutions of the salt in accordance with the present invention will ideally contain the salt at a concentration of 1 mg/ml to 290 mg/ml, preferably from 10 mg/ml to 190 mg/ml.

For intranasal administration, the salt of the present invention may conveniently be presented in unit dose form. A convenient unit dose formulation for intranasal administration contains the active ingredient in an amount of from 0.1 mg to 100 mg, suitably in the range of 1 to 60 mg, preferably 2 to 40 mg, which may be administered to either one or both nostrils. Ideally, 1 mg to 35 mg of the active ingredient is administered in a single dose to one nostril.

A typical unit dose formulation may be provided as a single dose in a sealed unit, for example a vial of glass or plastics material which may be filled and sealed using conventional manufacturing techniques. Alternatively, a sealed vial of plastics material may be produced by form-fill-seal technology. Ideally the vial and the components of the pharmaceutical formulation filled therein are heat stable. The sealed vial may be sterilised, for example by autoclaving at 121° C. for not less than 15 minutes, or alternatively by gamma irradiation of the container followed by sterile filtration of the solution, to provide a sterile unit dosage vial which can be assembled into a convenient delivery device prior to use. Preferably the unit dose volume is 50 to 200 μl, for example 100 μl.

Preferred devices for administering the intranasal formulation according to the invention include the Bespak multidose device, obtainable from Bespak, Kings Lynn, United Kingdom; and, in particular, the Valois "Monospray" single dose spray device as described, for example, in WO-A-93/00172.

According to a further aspect, the present invention provides a process for the preparation of the sulphate salt of formula I as defined above or a solvate thereof, which process comprises reacting N,N-dimethyl-2-[5-(1,2,4-triazol-1-ylmethyl)-1H-indol-3-yl]ethylamine of structural formula II:

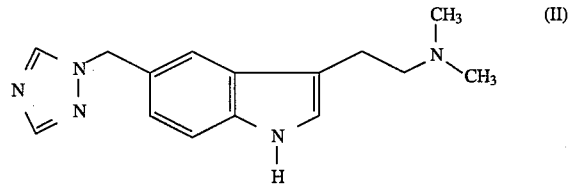

with approximately 0.5 molar equivalents of sulphuric acid in a suitable solvent.

The process is advantageously carried out by stirring the reactants at room temperature in an aqueous medium, typically in the presence of a lower alkanol such as ethanol or isopropyl alcohol.

The salt of formula I above or a solvate thereof may also be prepared by salt exchange, which comprises treating a salt of the compound of formula II above, other than the sulphate salt (2:1) of formula I, with a suitable sulphate salt.

Examples of appropriate sulphate salts which may be utilised in the above salt exchange procedure include metal sulphates, such as sodium sulphate or silver sulphate, and sulphated ion exchange resins. The reaction is conveniently carried out in an aqueous medium.

The compound of formula II above may be prepared by any one of a variety of procedures which will be readily apparent to the person skilled in the art. Since the compound of formula II contains an indole nucleus, a suitable method for its preparation is the familiar Fischer indole synthesis. This may be conveniently effected by reacting the hydrazine derivative of formula III:

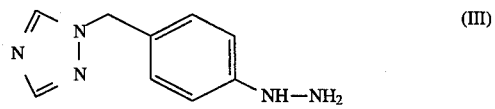

with the compound of formula IV:

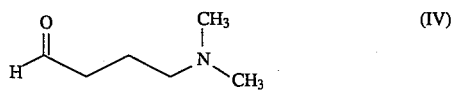

or a carbonyl-protected form thereof.

Suitable carbonyl-protected forms of the compound of formula IV include the dimethyl and diethyl acetal derivatives.

The reaction is conveniently carried out by stirring the reactants in the presence of 4% sulphuric acid at an elevated temperature, typically about 90° C.

The hydrazine derivative of formula III may be prepared from the corresponding aniline of formula V:

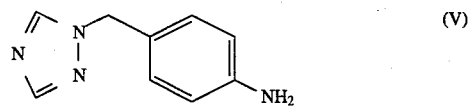

by diazotisation followed by reduction. Diazotisation is conveniently effected using sodium nitrite/conc. HCl and the resulting diazo product reduced in situ using, for example, tin(II) chloride/conc. HCl, sodium sulphite/conc. HCl or sodium sulphite/conc. $H_2SO_4$.

The aniline derivative of formula V may be prepared by reduction of the corresponding nitro compound of formula VI:

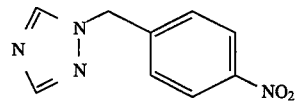

typically by transfer hydrogenation using a hydrogenation catalyst such as palladium on charcoal in the presence of a hydrogen donor such as ammonium formate, or alternatively by conventional catalytic hydrogenation or using tin(II) chloride.

The nitro compound of formula VI may conveniently be prepared by reacting the sodium salt of 1,2,4-triazole with a nitrobenzyl halide, e.g. 4-nitrobenzyl bromide, suitably in N,N-dimethylformamide at room temperature. Alternatively, compound VI may be prepared by reacting a nitrobenzyl halide, e.g. 4-nitrobenzyl bromide, with 4-amino-1,2,4-triazole, followed by deamination of the resulting triazolium salt by treatment with nitrous acid and subsequent neutralisation. This latter transformation, which may be accomplished in two separate steps or advantageously as a "one-pot" procedure with both steps combined, is conveniently effected using reaction conditions analogous to those described in *J. Org. Chem.*, 1989, 54, 731.

In a still further aspect, the present invention provides a method for the treatment and/or prevention of clinical conditions for which a selective agonist of 5-$HT_1$-like receptors is indicated, which method comprises administering to a patient in need of such treatment an effective amount of the salt of formula I as defined above or a pharmaceutically acceptable solvate thereof. In a particular embodiment of the method according to the invention, the salt of formula I or its pharmaceutically acceptable solvate is administered in the form of a solution, preferably an aqueous solution adapted for intranasal administration.

The present invention also provides the use of the salt of formula I as defined above or a pharmaceutically acceptable solvate thereof for the manufacture of a medicament, suitably a solution and preferably an aqueous solution adapted for intranasal administration, for the treatment and/or prevention of clinical conditions for which a selective agonist of 5-$HT_1$-like receptors is indicated.

The following non-limiting Examples are intended to illustrate the present invention.

PREPARATION 1

Step (i): 1-(4-Nitrobenzyl)-4-amino-4H-1,2,4-triazolium bromide

A mixture of 4-amino-1,2,4-triazole (250 g, 2.976 moles) and 4-nitrobenzyl bromide (ex Janssen, 99%, 617.5 g, 2.83 moles) in isopropyl alcohol (5.66 l) was brought to reflux with stirring. The mixture became a solution and then, almost immediately, the required triazolium salt crystallised out at reflux. The mixture was stirred and heated under reflux for 7.5 hours and then allowed to cool to room temperature overnight. Next day, the mixture was cooled to 0°–5° C., held for 1 hour and the product filtered, washed with a little isopropyl alcohol and then dried, in vacuo at 50° C. to give the title triazolium salt (808 g) in 95% yield as a white solid, m.p. 199° C. (dec.).

Step (ii): 1-(4-Nitrobenzyl)-1,2,4-triazole

A solution of sodium nitrite (206 g, 2.98 moles) in water (840 ml) was added subsurface over 70 minutes to a suspension of the preceding triazolium salt (808 g, 2.69 moles) in water (5.6 l) and conc. hydrochloric acid (505 ml) at 0°–5° C. The pale yellow slurry was stirred at <5° C. for 15 minutes and then allowed to warm to 25° C. over 1 hour. The colourless solution was adjusted to pH 9 by addition of aqueous ammonia solution (380 ml, 18N) maintaining the temperature <30° C. The mixture was cooled to 0°–5° C. and stirred for 1 hour. The solid was collected by filtration, washed with water (400 ml) containing aqueous ammonium hydroxide (20 ml, 18N) and dried under reduced pressure at 50° C. to give 535 g (97% yield) of the title nitro compound, m.p. 102°–103° C.

Step (iii): 1-(4-Aminobenzyl)-1,2,4-triazole

The preceding nitro compound (803 g, 3.9 moles), ammonium formate (1.16 kg, 18.4 moles) and 10% Pd/C (28 g) in methanol (8 l) was stirred under a nitrogen atmosphere and warmed to 30° C. Heating was discontinued and cooling applied to control the exothermic reaction by maintaining the temperature at 35°–45° C. for 2 hours. The reaction mixture was cooled at 20° C. and the catalyst removed by filtration through Hyflo filter aid. The filter pad was washed with methanol (2 l). The filtrate was concentrated and the residue diluted with ethyl acetate (12 l) and water (1.57 l). The lower aqueous layer was treated with aqueous ammonium hydroxide solution (10 ml, 18N) to pH 9. The aqueous layer was separated and extracted with ethyl acetate (2×6 l and 3 l). The combined extract was washed with saturated aqueous sodium hydrogen carbonate solution (1.57 l), dried and evaporated under reduced pressure to give 679 g (99% yield) of the title amine, m.p. 127°–28° C.

Step (iv): N,N-Dimethyl-2-[5-(1,2,4-triazol-1-ylmethyl)-1H-indol-3-yl]ethylamine A solution of sodium nitrite (16.7 g, 0.24 mole) in water (22.7 ml) was added subsurface to a solution of the preceding amine (40 g, 0.23 mole) in hydrochloric acid (65.3 ml) and water (162 ml) maintaining the temperature <5° C. The solution was stirred at 0°–5° C. for 1 hour. The solution was added to a suspension of sodium sulphite (72.4 g, 0.57 mole) in water (227 ml) cooled at 5°–10° C. under a nitrogen atmosphere. The red solution was stirred at 5°–10° C. for 10 minutes, allowed to warm to 20° C. over 20 minutes and then heated to 70° C. over 45 minutes. The solution was stirred at 70° C. for 2.5 hours and cooled to 65° C. Concentrated sulphuric acid (56.8 ml) was added to the solution over 15 minutes maintaining the temperature at 70°–80° C. The solution was stirred at 70° C. under a nitrogen atmosphere for 2 hours and then allowed to cool to 20° C. overnight. The solution of the resulting hydrazine was warmed to 25° C. and 4-(N,N-dimethylamino)-1,1-dimethoxybutane (44.3 g, 0.28 mole) was added over 15 minutes maintaining the temperature <35° C. The solution was stirred at 30°–35° C. for 30 minutes. The mixture was heated to 90° C. over 30 minutes and maintained at 90°–93° C. for 15 minutes. The mixture was cooled to 15° C. and Hyflo filter aid (68 g) added followed by aqueous ammonium hydroxide (200 ml, 18N) to adjust the pH to 11–12. The mixture was filtered and the filtrate and the Hyflo extracted with ethyl acetate (5×300 ml). The extract was dried ($Na_2SO_4$) and evaporated under reduced pressure. The residue was chromatographed on silica (550 g) with ethyl acetate:methanol (80:20) changing to ethyl acetate:methanol (50:50). The fractions containing product were evaporated under reduced pressure to give 27.8 g (45% yield) of the title compound in free base form.

EXAMPLE 1

N,N-Dimethyl-2-[5-(1,2,4-triazol-1-ylmethyl)-1H-indol-3-yl]ethylamine. 0.5 sulphate. 0.7 hydrate Sulphuric acid (1N, 1.17 ml) was added to a stirred solution of N,N-dimethyl-2-[5-(1,2,4-triazol-1-ylmethyl)-1H-indol-3-yl]ethylamine (0.63 g, 2.34 mmole) in water (0.73 ml) and isopropyl alcohol (15.9 ml). The mixture was seeded, then cooled to 0° C. The reaction mixture was filtered and the solid product washed with diethyl ether (100 ml) and then dried at 60° C. in vacuo to give the title 0.5 sulphate salt (0.68 g), m.p. 233°–234° C. (Found: C, 54.45; H, 6.35; N, 21.23; S, 4.66%. $C_{15}H_{19}N_5 \cdot 0.5\, H_2SO_4 \cdot 0.7\, H_2O$ requires C, 54.43; H, 6.52; N, 21.16; S, 4.84%).

EXAMPLE 2

Buffered sublingual tablet containing 50 μg (expressed as free base) of active ingredient

| | |
|---|---|
| N,N-dimethyl-2-[5-(1,2,4-triazol-1-ylmethyl)-1H-indol-3-yl]ethylamine. 0.5 sulphate. 0.7 hydrate | 0.056 mg |
| Avicel PH 200 | 91.194 mg |
| Starch 1500 | 22.0 mg |
| Sodium bicarbonate | 67.5 mg |
| Anhydrous sodium carbonate | 20.0 mg |
| Blue FD&C No. 2 Aluminium Lake | 0.55 mg |
| Saccharin sodium | 11.0 mg |
| Peppermint NAEFCO/P05.51 | 6.6 mg |
| Magnesium stearate | 1.1 mg |
| Total weight | 220.0 mg |

All the ingredients except magnesium stearate were mixed together in a suitable blender. The resulting mixture was then lubricated with magnesium stearate and compressed on a tablet press.

EXAMPLE 3

Buffered sublingual tablet containing 20 mg (expressed as free base) of active ingredient

| | |
|---|---|
| N,N-dimethyl-2-[5-(1,2,4-triazol-1-ylmethyl)-1H-indol-3-yl]ethylamine. 0.5 sulphate. 0.7 hydrate | 22.34 mg |
| Avicel PH 200 | 68.91 mg |
| Starch 1500 | 22.0 mg |
| Sodium bicarbonate | 67.5 mg |
| Anhydrous sodium carbonate | 20.0 mg |
| Blue FD&C No. 2 Aluminium Lake | 0.55 mg |
| Saccharin sodium | 11.0 mg |
| Peppermint NAEFCO/P05.51 | 6.6 mg |
| Magnesium stearate | 1.1 mg |
| Total weight | 220.0 mg |

All the ingredients except magnesium stearate were mixed together in a suitable blender. The resulting mixture was then lubricated with magnesium stearate and compressed on a tablet press.

EXAMPLES 4 AND 5

Sterile intranasal formulation

| | Example 4 | Example 5 |
|---|---|---|
| Compound of formula (II) | 0.85 mg | 170 mg |
| Sulphuric Acid (concentrated) BP | 0.155 mg | 30.9 mg |
| Bulk Water for Injections Ph. Eur. | to 1 ml | to 1 ml |

The compound of formula (II) is dissolved in the sulphuric acid previously diluted with water. The solution is made up to volume.

The solution may be packaged for intranasal administration, for example by filling into vials, sealing and sterilising the vials by autoclaving at 121° C. for not less than 15 minutes, or sterilised by filtration and aseptically transferred into sterile containers.

EXAMPLES 6 AND 7

Preserved intranasal formulation

| | Example 6 | Example 7 |
|---|---|---|
| Compound of formula (II) | 0.85 mg | 170 mg |
| Sulphuric Acid (concentrated) BP | 0.155 mg | 30.9 mg |
| Phenylethyl Alcohol USP | 4.0 mg | 4.0 mg |
| Benzalkonium Chloride USNF | 0.2 mg | 0.2 mg |
| Purified Water B.P. | to 1 ml | to 1 ml |

The compound of formula (II) is dissolved in the sulphuric acid previously diluted with water. Phenylethyl alcohol and benzalkonium chloride are added and the solution made up to volume.

In a similar manner further preserved formulations were prepared containing 1, 5, 10, 50, 80, 100 and 150 mg/ml of the compound of formula (II).

Formulations can be administered in unit dose volumes of 100 μl to either one or both nostrils of patients suffering from a moderate or severe migraine attack to deliver a dose of 0.1, 1, 5, 10 or 17 mg of the compound of formula (II).

EXAMPLES 8 AND 9

Sterile intranasal formulation

|  | Example 8 | Example 9 |
|---|---|---|
| Compound of formula (I) | 1 mg | 200 mg |
| Bulk Water for Injections Ph. Eur. | to 1 ml | to 1 ml |

The compound of formula (I) is dissolved in water and the solution made up to volume.

The solution may be packaged for intranasal administration, for example by filling into vials, sealing and sterilising the vials by autoclaving at 121° C. for not less than 15 minutes, or sterilised by filtration and aseptically transferred into sterile containers.

EXAMPLES 10 AND 11

Alternative preserved intranasal formulation

|  | Example 10 | Example 11 |
|---|---|---|
| Compound of formula (I) | 1 mg | 200 mg |
| Benzethonium Chloride | 0.2 mg | 0.2 mg |
| Purified Water B.P. | to 1 ml | to 1 ml |

The compound of formula (I) is dissolved in water. Benzethonium chloride is added and the solution made up to volume.

EXAMPLES 12 TO 15

Sterile intranasal formulation

|  | Example 12 | Example 13 | Example 14 | Example 15 |
|---|---|---|---|---|
| Compound of formula (II) | 5 mg | 50 mg | 100 mg | 160 mg |
| Sulphuric Acid (conc.) BP | 0.91 mg | 9.1 mg | 18.2 mg | 29.1 mg |
| Bulk Water for Injections Ph. Eur. | to 1 ml | to 1 ml | to 1 ml | to 1 ml |

The compound of formula (II) is dissolved in the sulphuric acid previously diluted with water. The solution is made up to volume.

The formulations are filled into vials in 100 μl aliquots, the vials are sealed and are sterilised by autoclaving at 121° C. for not less than 15 minutes. Alternatively the solutions may be sterilised by filtration and filled aseptically into sterile vials.

The formulations are administered in unit dose volumes of 100 μl to a single nostril of patients suffering from a moderate or severe migraine attack to deliver a dose of 0.5, 5, 10 or 16 mg of the compound of formula (II).

EXAMPLES 16 AND 17

Sterile intranasal formulation

|  | Example 16 | Example 17 |
|---|---|---|
| Compound of formula (II) | 160 mg | 160 mg |
| Sulphuric Acid (conc.) BP | 29.1 mg | 29.1 mg |
| Sodium Saccharin BP | 10 mg | 20 mg |
| Bulk Water for Injections Ph. Eur. | to 1 ml | to 1 ml |

The compound of formula (II) is dissolved in the sulphuric acid previously diluted with water. The solution is made up to approximately 90% of volume and the saccharin dissolved therein and the solution finally made up to volume.

The formulations are filled into vials in 100 μl aliquots, the vials are sealed and are sterilised by autoclaving at 121° C. for not less than 15 minutes. Alternatively the solutions may be sterilised by filtration and filled aseptically into sterile vials.

The formulations are administered in unit dose volumes of 100 μl to a single nostril of patients suffering from a moderate or severe migraine attack to deliver a dose of 16 mg of the compound of formula (II).

We claim:

1. The sulphate salt of N,N-dimethyl-2-[5-(1,2,4-triazol-1-ylmethyl)-1H-indol-3-yl]ethylamine.

2. N,N-Dimethyl-2-[5-(1,2,4-triazol-1-ylmethyl)-1H-indol-3-yl]ethylamine sulphate salt (2:1) of structural formula I:

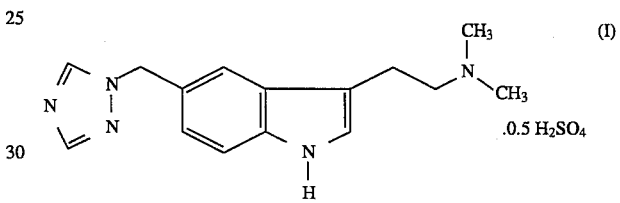

3. A hydrate of the salt according to claim 2.

4. The 0.7 hydrate of the salt according to claim 2.

5. A pharmaceutical composition comprising an effective amount of the salt according to claim 1 in association with one or more pharmaceutically acceptable carriers.

6. A pharmaceutical composition in solid form adapted for sublingual administration, comprising an effective amount of the salt according to claim 1; one or more pharmaceutically acceptable buffering agents capable of imparting to the buccal cavity following administration a pH of at least 7.5; and one or more pharmaceutically acceptable excipients.

7. A pharmaceutical composition adapted for intranasal administration comprising an effective amount of the salt according to claim 1 in association with one or more pharmaceutically acceptable carriers.

8. A composition according to claim 7 which is presented in the form of an aqueous solution.

9. A composition according to claim 8 which is presented in the form of a solution in sterile, pyrogen-free water.

10. A composition according to claim 8 containing the salt at a concentration of 1 mg/ml to 200 mg/ml.

11. A composition according to claim 10 containing the salt at a concentration of 10 mg/ml to 190 mg/ml.

12. A composition according to claim 11 containing the salt at a concentration of approximately 189 mg/ml.

13. A composition according to claim 7 presented in unit dosage form and containing the active ingredient in an amount of from 0.1 mg to 100 mg.

14. A composition according to claim 13 wherein the unit dose volume is 50 to 200 μl.

15. A method for the treatment of migraine and associated conditions for which a selective agonist of 5-HT$_1$-like receptors is indicated, which method comprises administering to a patient in need of such treatment an effective amount of the salt according to claim 1.

* * * * *